(12) United States Patent
Yacoub

(10) Patent No.: US 10,671,632 B1
(45) Date of Patent: Jun. 2, 2020

(54) AUTOMATED PIPELINE

(71) Applicant: CB Therapeutics, Inc., Carlsbad, CA (US)

(72) Inventor: Tyrone Jacob Yacoub, San Diego, CA (US)

(73) Assignee: CB THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 16/558,909

(22) Filed: Sep. 3, 2019

(51) Int. Cl.
| | | |
|---|---|---|
| G01N 33/48 | (2006.01) |
| G06F 16/25 | (2019.01) |
| G06F 16/903 | (2019.01) |
| G16B 50/00 | (2019.01) |
| G16B 40/00 | (2019.01) |
| G16B 30/20 | (2019.01) |
| G06F 16/9038 | (2019.01) |

(52) U.S. Cl.
CPC ........ *G06F 16/258* (2019.01); *G06F 16/9038* (2019.01); *G06F 16/90335* (2019.01); *G16B 30/20* (2019.02); *G16B 40/00* (2019.02); *G16B 50/00* (2019.02)

(58) Field of Classification Search
None
See application file for complete search history.

(56) References Cited

U.S. PATENT DOCUMENTS

| | | |
|---|---|---|
| 2005/0197784 A1 | 9/2005 | Kincaid et al. |
| 2014/0236607 A1 | 8/2014 | Alexandre |
| 2015/0112602 A1 | 4/2015 | Kural et al. |
| 2017/0132357 A1 | 5/2017 | Brewerton et al. |
| 2017/0286594 A1 | 10/2017 | Reid et al. |
| 2018/0314793 A1* | 11/2018 | Gross ............. C12Q 1/689 |

FOREIGN PATENT DOCUMENTS

| | | |
|---|---|---|
| CN | 107437004 A1 | 12/2017 |
| WO | WO2003065282 A1 | 8/2003 |
| WO | WO2013044354 A1 | 4/2013 |
| WO | WO2014052909 A2 | 4/2014 |
| WO | WO2014149972 A1 | 9/2014 |
| WO | WO2015027085 A1 | 2/2015 |
| WO | WO2015124600 A1 | 8/2015 |
| WO | WO2015171660 A1 | 11/2015 |

OTHER PUBLICATIONS

Nagasaki et al. "DDBJ Read Annotation Pipeline: A Cloud Computing-Based Pipeline for High-Throughput Analysis of Next-Generation Sequencing Data" (DNA Research, vol. 20 (2013) pp. 383-390).*

* cited by examiner

Primary Examiner — Anna Skibinsky
(74) Attorney, Agent, or Firm — Torrey Pines Law Group, PC

(57) ABSTRACT

The methods and system disclose an automated pipeline which receives a list of Accession IDs corresponding to transcriptomic, proteomic, genomic, or metabolomic data. Each Accession ID is submitted in parallel, launching a specific cloud computer to carry out a customized, fully automated transcriptome assembly (or proteomic assembly or genome assembly or metabolome assembly) and analysis by the automated pipeline. The output from multiple assemblies is automatically compiled and compared with genes of interest to identify new gene variants. The new gene variants can be used as queries by the automated pipeline to: discover variants of the variants; and determine new studies to analyze.

20 Claims, 7 Drawing Sheets

600A

Transcriptome Assembly Pipeline

Enter Accession IDs (comma separated)

ERR1924220, ERR1924219, ERR1924221

[Assemble Transcriptomes]

Warning: Read Length 50.0 < 90 for Accession ID ERR1924220

Warning: Read Length 50.0 < 90 for Accession ID ERR1924219

Warning: Read Length 50.0 < 90 for Accession ID ERR1924221

| DatePublished | Species | SpeciesAbb | RunAbb | Strategy | Source | Layout | TaxID |
|---|---|---|---|---|---|---|---|
| 2017-08-10 | Homo sapiens | Hsapiens | Hsapiens_1 | RNA-Seq | TRANSCRIPTOMIC | SINGLE | 9606 |
| 2017-08-10 | Homo sapiens | Hsapiens | Hsapiens_2 | RNA-Seq | TRANSCRIPTOMIC | SINGLE | 9606 |
| 2017-08-10 | Homo sapiens | Hsapiens | Hsapiens_3 | RNA-Seq | TRANSCRIPTOMIC | SINGLE | 9606 |

600B

| QueryID | SubjectID | AssemblyName | ID% | MatchCoverage | CoverID | GeneCoverage | HasGene | GeneLength |
|---|---|---|---|---|---|---|---|---|
| HomoSapiens_USP30 | Hsapiens_2_transcript15926 | Hsapiens_2 | 99.010 | 100.000 | 99.010 | 0.000000 | False | 0 |
| HomoSapiens_USP30 | Hsapiens_2_transcript3729 | Hsapiens_2 | 46.382 | 95.040 | 44.385 | 108.910891 | True | 110 |
| HomoSapiens_USP30 | Hsapiens_3_transcript1039 | Hsapiens_3 | 47.500 | 78.218 | 37.164 | 0.000000 | False | 0 |
| HomoSapiens_USP30 | Hsapiens_1_transcript1252 | Hsapiens_1 | 34.593 | 84.673 | 29.292 | 0.000000 | False | 0 |
| HomoSapiens_USP30 | Hsapiens_3_transcript6136 | Hsapiens_3 | 28.474 | 96.062 | 27.431 | 103.960396 | True | 105 |
| HomoSapiens_USP30 | Hsapiens_1_transcript0185 | Hsapiens_1 | 34.296 | 68.317 | 23.423 | 235.643564 | True | 238 |
| HomoSapiens_USP30 | Hsapiens_3_transcript13129 | Hsapiens_3 | 32.222 | 94.059 | 20.906 | 0.000000 | False | 0 |
| HomoSapiens_USP30 | Hsapiens_1_transcript7347 | Hsapiens_1 | 23.077 | 55.594 | 12.827 | 130.727273 | True | 911 |
| HomoSapiens_USP30 | Hsapiens_2_transcript8893 | Hsapiens_2 | 31.012 | 38.701 | 12.334 | 137.662338 | True | 930 |
| HomoSapiens_USP30 | Hsapiens_1_transcript6573 | Hsapiens_1 | 21.224 | 55.594 | 11.797 | 0.000000 | False | 0 |

FIG. 6

AUTOMATED PIPELINE

CROSS-REFERENCE TO RELATED APPLICATIONS

Not Applicable.

FIELD

The methods and systems of this invention support an automated pipeline for the collection, storage, processing, quality control, and analysis of biological datasets. The automated data pipeline leads to the automated discovery of novel biological molecules within assembled compilations (e.g., transcriptomes (RNA), proteomes (protein), genomes (DNA), and metabolomes (metabolites)).

INTRODUCTION

Compilations of biological molecules (e.g., transcriptomes (RNA), proteomes (protein), genomes (DNA), and metabolomes (metabolites)) reflect complex systems that can exhibit dynamic behaviors. The dynamic behaviors impact the properties of the biological molecules, which makes the investigation of the biological molecules a non-trivial task. For example, transcriptomes are collections of unique messenger RNA (mRNA) transcripts that vary across organisms and environmental conditions, wherein the organisms contain expressed genes (i.e., transcription of a genome's DNA code into mRNA). The mRNA is subsequently translated into proteins that may regulate functions within an organism's cells. According to environmental conditions or cellular states, some genes are: (i) expressed more frequently than others; and (ii) expressed at different times. Furthermore, the regulation of gene expression is a complex process with biological and medicinal implications.

The DNA sequences of the transcriptome can be used to identify the regions/parts of the genome used to code for active genes. Genes or variants of gene(s) implicated in biological processes can be identified by sequencing several transcriptomes under different growth or environmental conditions. Computer software is often used to scan multiple sequence alignments for single nucleotide polymorphisms (SNPs), wherein the SNPs may construct a panel of markers and be placed to a relative chromosomal location. Sequence alignments may also be used to find variants of known genes.

For a given species, voluminous amounts of data must often be processed when investigating all variants for a gene. This is often tedious and computationally intensive.

SUMMARY

The present teachings include a method for parallel processing of raw data sets directed to complex systems. The method can include: connecting to databases containing the raw data sets; receiving a query for a term: identifying studies containing the term; extracting respective accession identifications from the identified studies; simultaneously submitting the respective accession identifications to respective cloud computing instances customized for each of the identified studies, and thereby triggering an assembly pipeline for outputting refinements for each of the studies; retrieving metadata from the accession identifications, wherein the metadata comprises one or more columns and error identifying commands in the one or more columns; sending the outputted refinements for each of the studies to respective cloud computing buckets; identifying gene variants from the term based on the outputted refinements; displaying the outputted refinements in the one or more columns in a graphical user-interface; and wherein the outputted refinements comprise transcriptomes, proteomes, genomes, and metabolomes.

In accordance with an aspect, the method when simultaneously submitting the respective accession identifications to the respective cloud computing instances customized for each of the identified studies can involve: converting the metadata into scripting parameters and hardware parameters and thereby customizing the assembly pipeline; and determining an ideal cloud computing instance for each of the identified studies.

In accordance with an aspect, the method when customizing the assembly pipeline can involve: processing scripts within the assembly pipeline in series: and sending the processed scripts to the ideal cloud computing instances.

In accordance with an aspect, the method when processing the scripts within the assembly pipeline in series can involve: downloading datasets; performing pre-processing steps; implementing a transcriptome assembly for generating transcriptomes; performing quality control functions on the downloaded datasets and the generated transcriptomes; and performing downstream analysis steps.

In accordance with an aspect, the downstream analysis steps can involve: detection of single copy orthologs, open reading frames (ORFs), gene quantification, and annotation.

In accordance with an aspect, the method when sending the outputted refinements for each of the studies to the respective cloud computing instances can involve: comparing predicted peptides to gene queries to identify the gene variants; sending the identified gene variants to the respective cloud computing buckets for storage: extracting metadata of the identified gene variants; validating the identified gene variants by three-dimensional (3D) modeling and experimental findings; and wherein the outputted refinements are transcriptomes.

In accordance with an aspect, the method when analyzing the identified gene variant can involve: combining the metadata of the identified gene variants and the analyzed identified gene variants with metadata of the transcriptomes; and thereby measuring quality of the transcriptomes.

In accordance with an aspect, the method when measuring the quality of the transcriptomes can involve: applying machine learning on the metadata of the identified gene variants; generating a model directed to un-analyzed transcriptomes using the applied machine learning: and selecting additional studies of interest based on the generated model.

In accordance with an aspect, the pre-processing steps can involve: unzipped version of the raw data, bad read removal, trim read adaptors, and formatted read names.

The present teachings include a system for parallel processing of raw data sets directed to complex systems. The system can include: a server; a computing device in communication with the server over a network, the computing device including a processor and a memory. The memory bearing computer executable code can be configured to perform the steps of: connecting to databases containing the raw data sets; receiving a query for a term; identifying studies containing the term; extracting respective accession identifications from the identified studies; simultaneously submitting the respective accession identifications to respective cloud computing instances customized for each of the identified studies, and thereby triggering an assembly pipeline for outputting refinements for each of the studies; retrieving metadata from the accession identifications, wherein the metadata comprises one or more columns and error identifying commands in the one or more columns; sending the outputted refinements for each of the studies to respective cloud computing buckets; identifying gene variants from the term based on the outputted refinements; displaying the outputted refinements in the one or more columns in a graphical user-interface; and wherein the outputted refinements comprise transcriptomes, proteomes, genomes, and metabolomes.

In accordance with an aspect, the system when simultaneously submitting the respective accession identifications to the respective cloud computing instances customized for each of the identified studies can involve: converting the metadata into scripting parameters and hardware parameters and thereby customizing the assembly pipeline; and determining an ideal cloud computing instance for each of the identified studies.

In accordance with an aspect, the system when customizing the assembly pipeline can involve: processing scripts within the assembly pipeline in series: and sending the processed scripts to the ideal cloud computing instances.

In accordance with an aspect, the system when processing the scripts within the assembly pipeline in series can involve: downloading datasets; performing pre-processing steps: implementing a transcriptome assembly for generating transcriptomes; performing quality control functions on the downloaded datasets and the generated transcriptomes; and performing downstream analysis steps.

In accordance with an aspect, the downstream analysis steps can involve: detection of single copy orthologs, open reading frames (ORFs), gene quantification, and annotation.

In accordance with an aspect, the system when sending the outputted refinements for each of the studies to the respective cloud computing instances can involve: comparing predicted peptides to gene queries to identify the gene variants; sending the identified gene variants to the respective cloud computing buckets for storage: extracting metadata of the identified gene variants; validating the identified gene variants by three-dimensional (3D) modeling and experimental findings; and wherein the outputted refinements are transcriptomes.

The present teachings include a computer program product for parallel processing of raw data sets directed to complex systems. The system can include computer executable code embodied in a non-transitory computer readable medium when executing on one or more computing devices. The steps can include: connecting to databases containing the raw data sets: receiving a query for a term; identifying studies containing the term; extracting respective accession identifications from the identified studies; simultaneously submitting the respective accession identifications to respective cloud computing instances customized for each of the identified studies, and thereby triggering an assembly pipeline for outputting refinements for each of the studies: retrieving metadata from the accession identifications, wherein the metadata comprises one or more columns and error identifying commands in the one or more columns: sending the outputted refinements for each of the studies to respective cloud computing buckets: identifying gene variants from the term based on the outputted refinements; displaying the outputted refinements in the one or more columns in a graphical user-interface; and wherein the outputted refinements comprise transcriptomes, proteomes, genomes, and metabolomes.

In accordance with an aspect, the system when simultaneously submitting the respective accession identifications to the respective cloud computing instances customized for each of the identified studies can involve: converting the metadata into scripting parameters and hardware parameters and thereby customizing the assembly pipeline: and determining an ideal cloud computing instance for each of the identified studies.

In accordance with an aspect, the system when customizing the assembly pipeline can involve: processing scripts within the assembly pipeline in series: and sending the processed scripts to the ideal cloud computing instance.

In accordance with an aspect, the system when processing the scripts within the assembly pipeline in series can involve: downloading datasets; performing pre-processing steps; implementing a transcriptome assembly for generating transcriptomes: performing quality control functions on the downloaded datasets and the generated transcriptomes: and performing downstream analysis steps.

In accordance with an aspect, the downstream analysis steps can include: detection of single copy orthologs, open reading frames (ORFs), gene quantification, and annotation.

These and other features, aspects, and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 6 depicts columns of metadata in a user interface.

DETAILED DESCRIPTION

Abbreviations and Definitions

Figure 1:
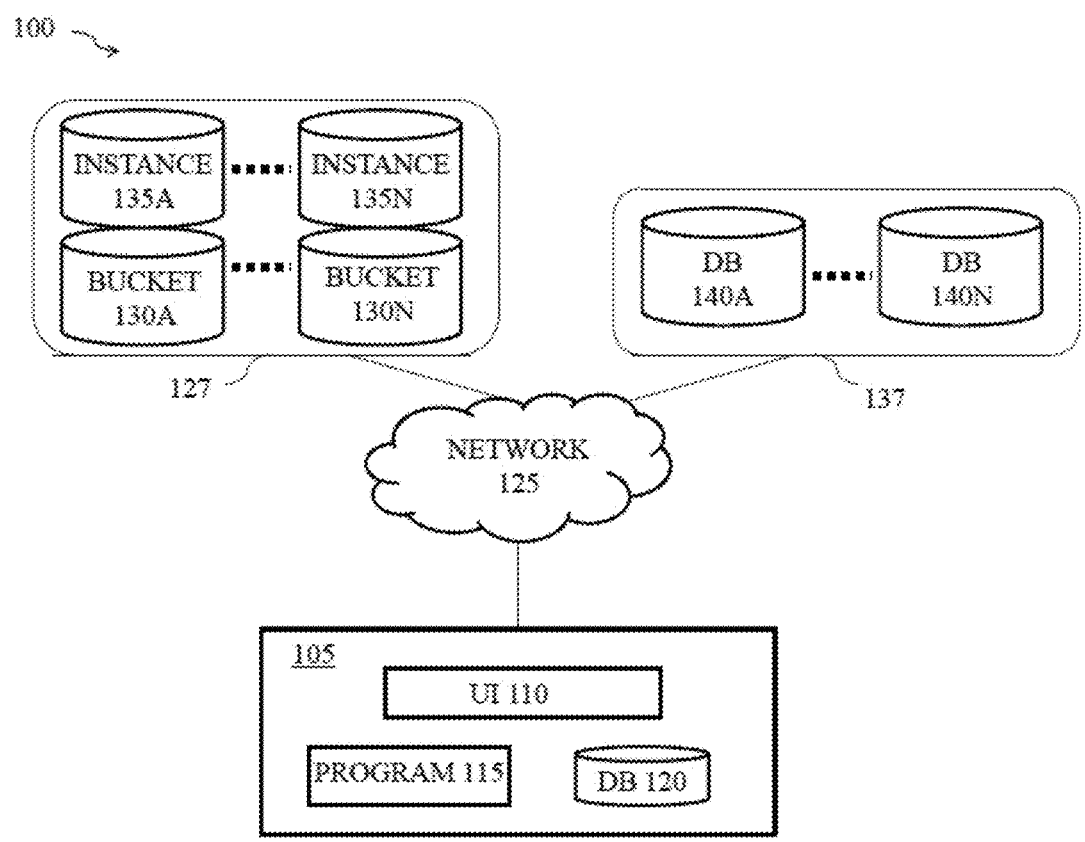
FIG. 1 depicts a computing environment for an automated pipeline involving the collection, storage, processing, quality control, and analysis of biological datasets.

To facilitate understanding of the invention, a number of terms and abbreviations as used herein are defined below as follows:

Assembly: As used herein, the term "assembly" refers to the process of taking raw DNA fragment "reads" and aligning the "reads" to find full-length transcripts.

Genes: As used herein, the term "genes" refer to a sequence of nucleotides in DNA or RNA that codes for a molecule that has a function.

Gene expression: As used herein, the term "gene expression" refers to processes by which information from a gene is used to synthesize ribonucleic acid (RNA).

Genome: As used herein, the term "genome" refers to the complete set of genes of an organism consisting of deoxyribonucleic acid (DNA). DNA has: (i) a coding region, which usually commences at the 5' end by a start codon and terminates at the 3' end with a stop codon: and (ii) a noncoding region.

Transcription: As used herein, the term "transcription" refers to responses to: (i) native biological and chemical processes for (a) expressing genes as messenger RNA (mRNA) molecules (transcripts) in proportion to the requirements of the cell, and (b) generally code for proteins: and (ii) environmental conditions, such as heat shock, starvation, and oxygen deprivation. One approach to investigating gene expression is to carry out laboratory experiments to extract the transcribed mRNA molecules from a cell and sequence them.

Transcriptome: As used herein, the term "transcriptome" refers to the complete set of transcribed mRNA molecules for a given organism in any one condition.

Reverse transcription: As used herein, "reverse transcription" refers to extracted mRNA molecules used to generate corresponding complementary DNA (cDNA) molecule via an enzyme. The cDNA can be sequenced in the same manner as determining the genome sequence.

De Novo Genome Assembly: As used herein, "de novo genome assembly" refers to a type of program that assembles short genomic nucleotide sequences into longer sequences without the use of a reference genome.

De Novo Transcriptome Assembly: As used herein, "de novo transcriptome assembly" refers to a de novo sequence assembly method for determining a transcriptome without the use of a reference genome.

Genome sequence coverage levels can vary as a result of repeat content in non-coding intron regions of DNA. Transcriptome sequence coverage levels can be directly indicative of gene expression levels.

Metabolome: As used herein, the term "metabolome" refers to the complete set of small-molecule chemicals for a biological sample. The biological sample can be a cell, a cellular organelle, an organ, a tissue, a biofluid, or an entire organism. The small molecule chemicals found in a given metabolome include: (i) endogenous metabolites naturally produced in an organism (e.g., amino acids, organic acids, nucleic acids, fatty acids, amines, sugars, vitamins, cofactors, pigments, antibiotics, and so forth); and (ii) exogenous metabolites not naturally produced in an organism (e.g., drug molecules, food additives, environmental contaminants, toxins, and xenobiotics). Metabolites which are considered part of the metabolomes are "small molecules" which have a molecular weight less than 1500 daltons (Da).

Macromolecules: As used herein, the term "macromolecules" refers to biopolymers, such as proteins, carbohydrates, lipids, ribonucleic acid (RNA), and deoxynucleic acid (DNA), which contains thousands of atoms or more and a molecular weight greater than 1500 daltons.

Syntax: As used herein, the term "syntax" refers to a set of rules that define the combination of symbols associated with a function. The syntax is the format of the code. After processing the syntax and the function, the meanings (or values) from the syntax are processed.

The invention is directed to a scalable, parallelized, and fully automated de novo transcriptome assembly.

The present invention is directed to methods and systems for an automated pipeline. The automated pipeline herein reduces the errors and time required for manually assembling and analyzing transcriptomes, proteomes, genomes, and metabolomes of interest.

Whereas the human time required for manual assembly of transcriptomes, genomes, and metabolomes scales with the number of assemblies, the automated pipeline herein can process and analyze any number of assemblies with only a list of accession identification numbers. This streamlining is accomplished by meticulous collection of metadata, transformation of metadata into software and hardware parameters, complex error-handling, selection of software libraries and bioinformatics tools which are most amenable to automation, and development of pipeline functions for seamless automation and processing of biological data through assembly stages to produce, e.g., a full transcriptome.

Additionally, the automated pipeline herein can quickly and efficiently discover gene variants in publicly available transcriptomic data, some of which are not discovered by standard transcript identifiers, such as Transdecoder. Thus, the automated pipeline herein can discover transcripts that are full genes (including start and stop codons) that not discovered by publicly available variant discovery tools, regardless of the transcriptome assembly methods. The automated pipeline herein is not limited to transcriptomic data, and can also be applied to proteomic, metabolomic, and genomic data.

Transcriptome assembly and analysis are painstaking processes that require several major steps (i.e. pre-processing, assembly, post-processing), each containing several minor steps, most of which require human input and are sensitive to the original format and location of the data in public repositories such as the National Center for Biotechnology Information (NCBI). In contrast, the automated pipeline herein is a tool of value to researchers by fully automating the discovery process. Additionally, the automated pipeline herein automatically processes multiple transcriptomes in parallel, requiring only a list of study accession IDs. For example, the automated pipeline herein enables a researcher with sufficient resources (e.g., estimate of $40/transcriptome) to effortlessly assemble and analyze any number of transcriptomes of interest to find gene variants, which would otherwise be prohibitively tedious and time-consuming. Thus, researchers pursue studies with a lower probability of expected discovery without the aid of automated pipeline herein.

Aspects of the present teachings may be further understood in light of the following Figures (FIG. 1-FIG. 7), which should not be construed as limiting the scope of the present teachings in any way.

As depicted in FIG. 1, a researcher assembles multiple transcriptomes from multiple databases and saves the output to multiple hard drives in the computing environment. The notation of a part number A-N, such as, for example, computers 130A-N, buckets 135A-N or databases 140A-N, indicate there can be one or more instances of cloud computers 130, one or more hard drives in the cloud 135 and one or more online databases 140.

As depicted in FIG. 1, computing environment 100 includes: device 105, cluster 127, and cluster 137, which are connected to each other by network 125. Network 125 can be telecommunications network listed in FIG. 7 below. Cluster 127 can be a cloud computing center (i.e., cloud computing resource) which contains computers 130A-N (i.e., a remote computer launched on demand and terminated after analysis is performed by program 115 in device 105) and hard drives 135A-N. Cloud computers 130A-N can also be referred to as cloud computing instances or instances. Cloud hard drives 135A-N can also be referred to as storage buckets or buckets. Cluster 137 can contain databases 140A-N. Databases (DBs) 140A-N are connected to web pages, multimedia content, web servers, and other web resources that can be accessed by network 125, such as the National Institute of Health (NIH) and the Protein Data Bank in Europe (PDe). Databases 140A-N are not limited to connections with the NIH and PDe. UI 110 can be a graphical user interface residing in device 105 for displaying the output, as processed and generated by program 115. In UI 110, program 115 receives an accession ID through a web application (i.e., a client-server computer program that the client runs in a web-browser), which initiates metadata collection and assembly by program 115. Program 115 in device 105 can send, retrieve, and extract contents from database (DB) 120 in device 105, instances 130A-N and buckets 135A-N in cluster 127; and databases 140A-N in cluster 137.

Program 115 can contain or connect to tools used for automated pipeline herein in the assembly for transcriptomes. Program 115 uses tools for scripting, alignment, peptide detection, pre-processing, assembly, and postprocessing. Program 115 can be an automated transcriptome assembly pipeline existing as a collection of customizable code files and a cloud computer representation that contains numerous software packages. The customized cloud computers residing in cluster 127 are contained among instances 130A-N. The output can be stored in a hard drive in the cloud, which is contained among buckets 135A-N. As supported by the automated pipeline herein, program 115 performs the downstream transcriptome processing and gene variant discovery steps. These steps can be automated and applied to multiple transcriptomes in an automated fashion. The sole user input used by program 115 to select gene variants of interest can be a study accession identification number or list of accession identification numbers (IDs). For example, program 115 can receive a list of IDs and simultaneously assemble any number of transcriptomes (limited only by cloud resource availability), in a facile and automated manner, while reducing processing errors.

For example, program 115 can retrieve accession IDs via a user input query term (e.g. a species of interest). The resulting studies of interest, which contain transcriptomic and genomic data, can be identified from cluster 137. Program 115 can individually separate inputted study accession identification numbers and send the study accession identification numbers to respective cloud computing instances for performing the automated pipeline herein. Thus, transcriptomes and genomes can be analyzed simultaneously (or in parallel) on automatically customized cloud computing resources, wherein the cloud computing resources support the automated pipeline herein and analysis from a sole input of inputted study accession identification numbers. The input of the accession identification numbers leads to the following outputs: transcriptome, transcriptome assembly metadata, detection of single copy orthologs, open reading frames (ORFs), gene quantification, predicted peptides, annotation for all transcripts, gene variants, and gene variant metadata.

Program 115 can fully automate the identification or discovery of gene variants by using cutoffs or thresholds for gene variant attributes. The identification or discovery of gene variants by program 115 loops back to receiving gene queries, which can also be automated to iteratively search for gene variants of selected gene variants. The selection of future studies of interest via machine learning may be aided by the connection from identification/discovery of gene variants back to the step for predicting the quality of un-analyzed transcriptomes. Additionally, program 115 can be useful for large-scale data collection. Specific metadata (from the raw data or the assembly pipeline) can be correlated with the best results (most gene variants, highest quality assemblies). This can subsequently inform study selection in the next iteration, and thus program 115 can process an unlimited number of transcriptomes in parallel without expending extra effort by a researcher operating device 105. In contrast, arbitrary cutoffs based on relatively little experience—i.e. filtering NCBI studies, by "number reads>10 million"—can be obviated by using program 115. Stated another way, program 115 is a fully automated and scalable de novo assembly for transcriptomes. Program 115 contains automated pipeline functions where: (i) a number of transcriptomes can be analyzed simultaneously (in parallel) on automatically customized and launched cloud computers; and (ii) the entire assembly and analysis can be fully automated in the cloud for each transcriptome study.

Figure 2:
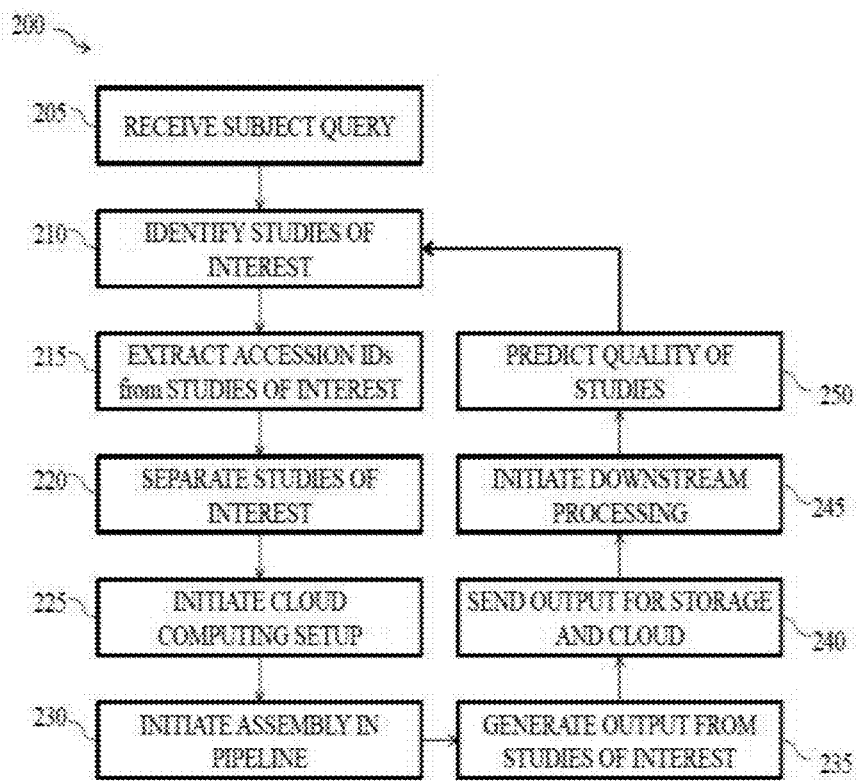
FIG. 2 depicts a flowchart for large-scale discovery of gene variants with parallelized transcriptome mining in cloud computing resources.
Figure 3:
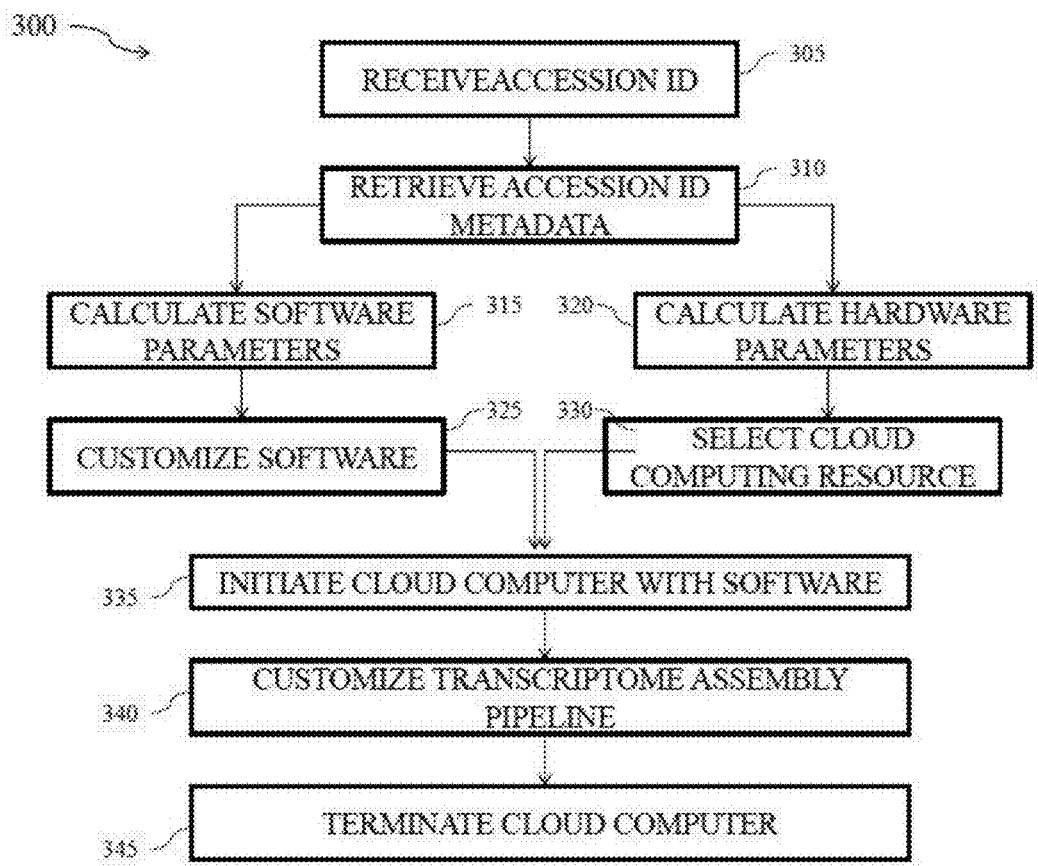
FIG. 3 depicts a flowchart for automated customization of software and automated selection of cloud computing resources.
Figure 4:
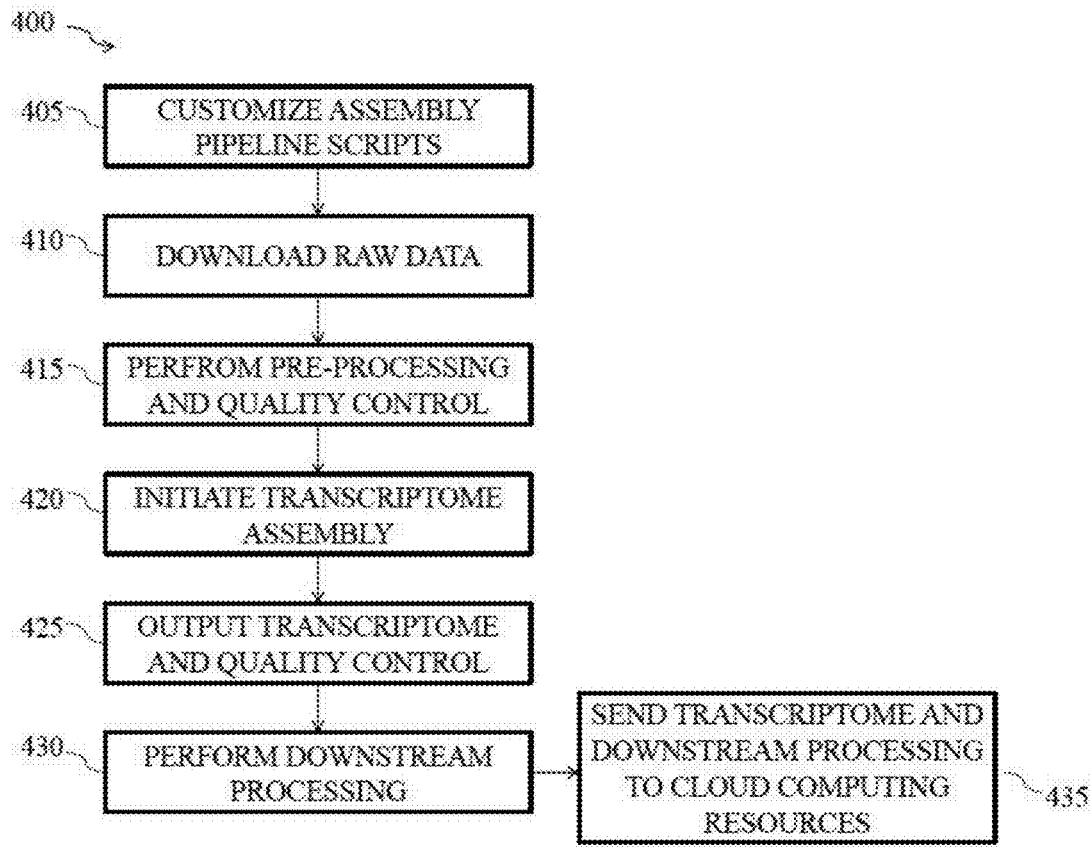
FIG. 4 depicts a flowchart for the launch of cloud computing resources for de novo transcriptome assembly.
Figure 5:
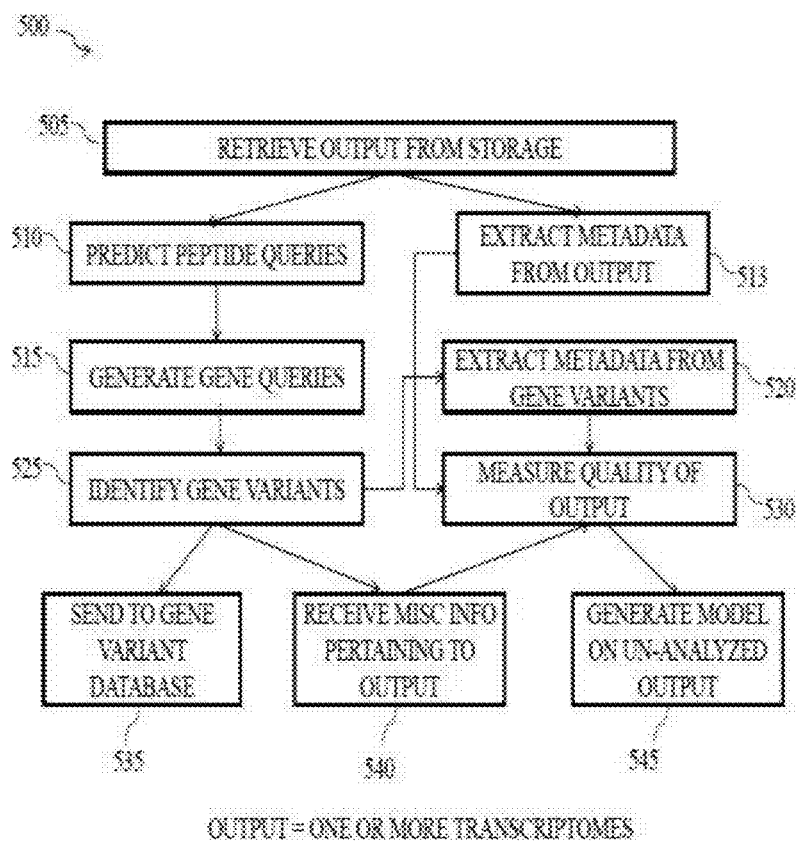
FIG. 5 depicts a flowchart for downstream processing of transcriptome assembly.

Program 115 performs the operational steps in flowchart 200 in FIG. 2, flowchart 300 in FIG. 3, flowchart 400 in FIG. 4, and flowchart 500 in FIG. 5. To perform these steps, program 115 receives data input(s). As described in more detail in the Examples section, A1 and A2 can be applied to data input(s) for full automation. A1 is a combination of: (i) customized code or syntax: and (ii) unmodified standard algorithms. A2 are modified standard algorithms, which have been customized based on the study.

Similarly, program 115 can be applied for proteomes, genomes, and metabolomes.

As depicted in FIG. 2, program 115 performs the steps in flowchart 200 for the large-scale discovery of gene variants with parallelized transcriptome mining in the cloud computing resources.

The automated pipeline herein begins with program 115 receiving a subject query in step 205. The subject query can be a list of Accession IDs either manually selected or determined automatically via a manually entered subject query (i.e. a species name). The subject query corresponds to unique sets for publicly available studies containing raw transcriptomic data. An Accession ID, as received on a local machine or a web application, such as, program 115 on device 105, can subsequently be processed by program 115 to identify studies of interest containing the Accession ID in step 210. In the automated pipeline herein, a combination of customized code or syntax and unmodified standard algorithms (A1) can be used by program 115 to: (i) extract the Accession IDs in each of the studies of interest in step 215; and (ii) separate studies of interest in step 220. Program 115 can initiate or launch cloud computing resources, such as cluster 127, in step 225. Program 115 can initiate assembly of the transcriptome (or proteome or genome or metabolome) in step 230. Program 115 can generate an output from studies of interest using the combination of customized code or syntax and unmodified standard algorithms (A1) in step 235. The output can be, but is not limited to, the following: (i) transcriptome: (ii) transcriptome assembly metadata: (iii) genome; (iv) genome assembly metadata: (v) gene quantification; (vi) quality control; (vii) predicted peptides: (viii) annotation for all transcripts; (ix) gene variants; and (x) gene variant metadata. Each study has an output, which can be sent to internal storage (e.g., database 120 in device 105) and the cloud in cluster 127. More specifically, raw, unstructured, and structured data used to derive the assembly of the transcriptome (or proteome or genome or metabolome) in the automated pipeline herein can be downloaded to database 120 in device 105. The contents for each study of studies 1-4 can be displayed in GUI 110. For example, studies 1-4 can be identified by program 115. The raw, unstructured, and structured data from studies 1-4 can be each individually separated, sorted, and displayed in GUI 110 in device 105. Each study can be sent to a bucket in cluster 127. For this example, program 115 can send: (i)

study 1 and the associated output to bucket 135A; (ii) study 2 and the associated output to bucket 135B; (iii) study 3 and the associated output to bucket 135C; and (iv) study 4 and the associated output to bucket 135D. Program 115 can: (i) initiate downstream processing in step 245; and (ii) predict the quality of the identified studies in step 250.

As depicted in FIG. 3, program 115 performs the operational steps in flowchart 300 for automated customization of software and automated selection of cloud computing resources.

In the automated pipeline herein, program 115 can: receive an accession ID in step 305; and retrieve accession ID metadata in step 310 in an automated fashion. Program 115 can retrieve the accession ID metadata by applying the combination of customized code or syntax and unmodified standard algorithms (A1) on the received data inputs, which is the accession ID from step 305.

Program 115 can convert the accession ID metadata into parameters for assembly scripts and cloud computing resources (e.g., cluster 127) by applying the combination of customized code or syntax and unmodified standard algorithms (A1) on the accession ID metadata. More specifically, program 115 can perform the following in an automated fashion: (i) calculating software parameters which correspond to assembly scripts in step 315: and (ii) calculating hardware parameters which correspond to cloud computing resources in step 320.

By calculating the software parameters for the automated pipeline herein, program 115 can determine and optimize parameters for the various stages of the assembly pipeline herein (e.g. pre-processing, assembly, post-processing) in step 325. The calculated software parameters can be used to customize the assembly pipeline software in an automated fashion in the automated pipeline herein. Based on the optimized parameters, program 115 selects the ideal cloud instance in cluster 127 in step 330 and initiates the ideal cloud instance in step 335.

Based on the customized assembly scripts, program 115 can customize the transcriptome assembly pipeline for the automated pipeline herein in step 340. More specifically, program 115 can run the customized assembly scripts for each study in series on cloud computing instances in an automated fashion.

When the output is generated, program 115 can send the output to the cloud storage buckets (among buckets 135A-N) in cluster 127. Each individual output can be sent to a respective cloud storage bucket (or bucket among buckets 135A-N). In response to program 115 sending the output to the cloud computing instances, program 115 instructs the cloud computing instances to save the output and thereby program 115 can terminate the cloud computing instances in an automated fashion in step 345.

As depicted in FIG. 4, program 115 performs the operational steps of flowchart 400 for the launch of cloud computing resources for de novo transcriptome assembly.

The automated pipeline herein can be a de novo transcriptome assembly pipeline, which is run completely in the cloud computing resources (e.g., cluster 127) without requiring human input. Program 115 can customize assembly pipeline scripts in an automated fashion in step 405. More specifically, program 115 can apply the combination of customized code or syntax and unmodified standard algorithms (A1) for: (i) the automated conversion of metadata to hardware and software parameters; and (ii) the automated launch of customized cloud instance.

Program 115 can customize scripts for transcriptome assembly using study-specific metadata. In turn, program 115 can use the combination of customized code or syntax and unmodified standard algorithms (A1) to perform the following in an automated fashion: (i) downloading raw data in step 410: and (ii) performing pre-processing and quality control in step 415. Pre-processing and quality control can involve but are not limited to: (i) command line syntax; (ii) unzipping raw data; (iii) removing bad reads: (iv) trimming read adaptors; and (v) applying quality control.

Program 115 uses a set of customization scripts if the source parameters are transcriptomic data.

Program 115 uses a set of customization scripts for a Bash profile.

Program 115 can initiate transcript assembly in step 420. The transcript assembly is a de novo transcript assembly, which can use modified standard algorithms that have been automatically customized based on the study (A2) and subsequently apply A2 on the received data sets. The received data sets have undergone pre-processing and quality control. Program 115 can generate a transcriptome in an automated fashion, based on the raw data that undergoes pre-processing and transcriptome assembly.

Program 115 can output the transcriptome and the quality control of the transcriptome to UI 110 in an automated fashion in step 425.

Program 115 can perform downstream processing in an automated fashion in step 430. More specifically, the modified standard algorithms that have been automatically customized based on the study (A2) can be applied on transcriptomes. In turn, program 115 can perform: single copy ortholog analysis; peptide detection; gene expression quantification; and transcript annotation.

Program 115 can send the transcriptome and resultant output from downstream processing to the cloud computing resources (e.g., cluster 127) in step 435 using the combination of customized code or syntax and unmodified standard algorithms (A1).

As depicted in FIG. 5, program 115 performs the operation steps of flowchart 500 for downstream processing of transcriptome assembly.

In the automated pipeline herein, program 115 can retrieve the output from storage, such as a bucket among buckets 135A-N at step 505. The output can be one or more transcriptomes. Using the combination of customized code or syntax and unmodified standard algorithms (A1) on the retrieved output, program 115 can: (i) predict peptide queries in step 510; and (ii) extract metadata from the output in step 513. More specifically, the output is one or more transcriptomes. In other embodiments, the output is one or more proteomes, one or more genomes, or one or more metabolomes. In response to program 115 predicting peptide queries in step 510, program 115 can generate gene queries in step 515.

Program 115 runs Transdecoder functions to detect open read frames and predict peptides.

Program 115 runs a program for: (i) clustering and comparing proteins and nucleotide sequences; (ii) determining if there are errors in the clustered and compared proteins and nucleotide sequences; and (iii) calculating coverage statistics for the coverage assembly scripts. Parameters are configured for a threshold, word size, memory, thread count, and description length.

Using the combination of customized code or syntax and unmodified standard algorithms (A1) on the gene queries, program 115 can: (i) identify gene variants in step 525; (ii) extract metadata from gene variants in step 520: (iii) send the identified gene variants to a gene variant database (e.g. a bucket among buckets 135A-N) in step 535; and (iv)

receive miscellaneous info pertaining the output in step 540. The miscellaneous info can include: (i) three-dimensional modeling of the one or more transcriptomes; and (ii) experimental validation and evaluation of the one or more transcriptomes including the performance of gene variants.

Using the combination of customized code or syntax and unmodified standard algorithms (A1) on: (i) the received miscellaneous info pertaining to the output; (ii) the metadata from the output; and (iii) the metadata from the gene variants, program 115 can measure the quality of the output in step 530, wherein the output are one or more transcriptomes. In other embodiments, the output is one or more proteomes, one or more genomes, or one or more metabolomes. The combination of customized code or syntax and unmodified standard algorithms (A1) on the measured quality of the output, program 115 can generate a model on un-analyzed output in step 545. The model is derived from machine learning to aid program 115 in selecting future studies of interest.

The machine learning for deriving the model can use a neural network. The neural network can include any combination of neural networks including, but not limited to, Perception Neural Network, Feed Forward Neural Network, Artificial Neuron, Deep Feed Forward Neural Network, Radial Basis Function Neural Network, Recurrent Neural Network, Long/Short Term Memory, Gated Recurrent Unit, Auto Encoder Neural Network, Variation AE Neural Network, Demising AE Neural Network, Sparse AE Neural Network, Markov Chain Neural Network, Modular Neural Network, Hopfield Network, Boltzmann Machine, Restricted BM Neural Network, Deep Belief Network, Deep Convolution Network, Deconvolutional Network, Deep Convolution Inverse Graphics Network, Generative Adversarial Network, Liquid State Machine Neural Network, Extreme Learning Machine Neural Network, Echo State Network. Deep Residual Network, Kohonen Self Organizing Neural Network, Support Vector Machine Neural Network, Neural Turing Machine Neural Network, Convolution Neural Networks such as LeNet, AlexNet, ZF Net, GoogLeNet, VGG Net, Microsoft ResNet, and Region Based CNNs including, but not limited to, Fast R-CNN, Faster R-CNN, R-FCN, Multibox, SSD, and YOLO, amongst others which are known to those of skill in the art.

Figure 7:
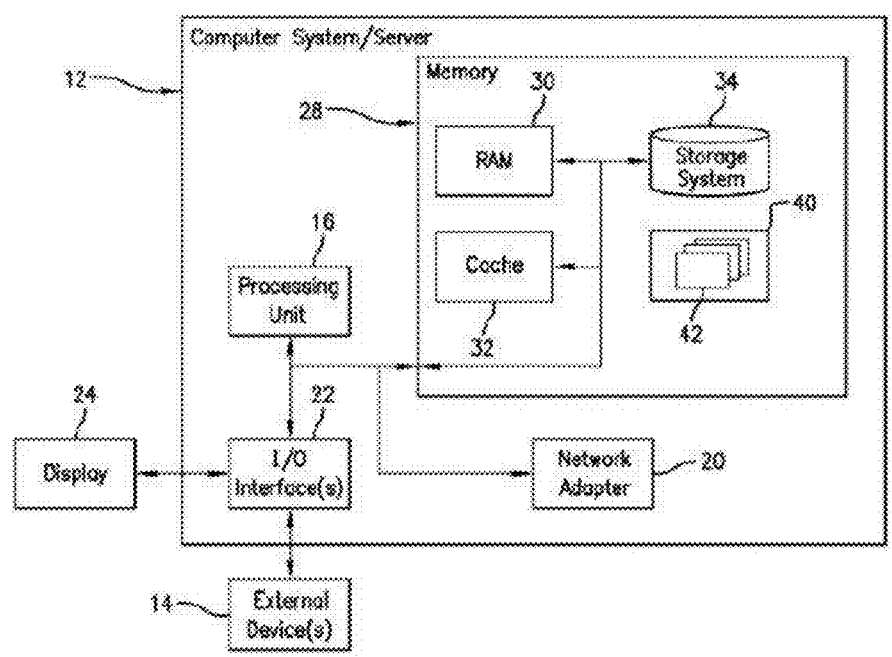
FIG. 7 depicts a device for implementing the flowcharts in methods and systems herein.

As depicted in FIG. 7, computer system/server 12 in computing node 10 is shown in the form of a general-purpose computing device 600. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM. DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14, such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical applications, or technical improvement over technologies found in the marketplace, or to enable others of ordinary skill in the art to understand the embodiments disclosed herein.

EXAMPLES

Aspects of the present teachings may be further understood in light of the following examples, which should not be construed as limiting the scope of the present teachings in any way. A1 includes the combination of: (i) syntax or code and (ii) unmodified standard algorithms, as referred to above. A2 includes modified standard algorithms based on identified studies. In the examples below, program 115 applies on data inputs via: (i) a singular use of A1 or A2; or (ii) dual use of A1 and A2.

Example 1—Syntax or Code for Extracting Metadata

Using a high-level and general-purpose programming language, program 115 imports software libraries for data manipulation and analysis. Additional software libraries are imported for making the machine-human interface for facile processing of inputs, performing mathematical functions, and documenting search queries. In turn, columns are automatically configured for sorting, compiling, and separating contents from a received input, such as an accession ID. A master metadata database is thus appended for each new study. The columns include three categories: (i) metadata taken directly from the internet: and (ii) metadata calculated using mathematical functions on metadata from (i).

Metadata taken directly from the internet includes, e.g. the following columns: 'Source', 'Selection', 'BioSample', 'Description', 'TaxID', 'Species', 'ProjectID', 'StudyID', 'Title', 'AccessionID', 'FileSize', 'DatePublished', and 'ReadLength'.

Program 115 retrieves above metadata using an automated web scraping function, where the accession ID is inserted into several URL addresses to retrieve all of the metadata of interest. The html retrieved from the URLs is debugged using a plurality of software libraries (i.e. A1 and A2). The html text is converted into a readable format to extract the metadata from table lines.

Program 115 defines functions to recognize and validate the format of metadata entries, including verification of the type (e.g., string or integer), string pattern (e.g., that the 'ProjectID' always begins with 'PRJ'), and category (e.g., 'Layout' equals 'Paired' or 'Single.')

Program 115 defines diagnostic functions to determine the quality of a study prior to assembly. For example, if 'GC_content' is not within the range [0.3, 0.7], or 'Bases(Gbp)' is not above 100M, program 115 warns the user that the data is of low quality.

Program 115 also defines functions to reformat some metadata entries, including numerical correction factors to ensure uniform units of measurement. Program 115 also defines functions to overcome inconsistencies in the organization of online metadata, such as adjusting the table line index according to the absence of certain entries. To catch and reduce processing errors and automate the functions performed by program 115, program 115 executes the following function for metadata entries:

```

def warn_if_unacceptable(column, how, acceptable_values):
    if how=='equals':
        if meta_dict[column] not in acceptable_values:
            print('Warning, { } "{ }" not in { } for id { }'.format
(column, meta_dict[column], acceptable_values, accession_id))
        return
    elif how=='begins with':
        for value in acceptable_values:
            if meta_dict[column][:len(value)]==value:
                return
        print('Warning, { } "{ }" does not begin with { } for id { }'.format(
column, meta_dict[column], acceptable_values, accession_id))
        return

```

Additional metadata for use in subsequent assembly stages is calculated based on the above scraped metadata using mathematical functions and heuristics, including the following calculated columns: 'MaxMemory', 'CPU', 'SpeciesAbb', and 'Runnabb'. Calculated column 'MaxMemory' is the memory required for processing the data in gigabytes. It is calculated based on a metadata entry (e.g. 'FileSize(GB)') and a transcriptome assembly heuristic (e.g. XGB RAM per GB file size). Calculated column 'CPUs' is the number of CPUs required for processing data. Calculated column 'SpeciesAbb' is the abbreviation for the species, calculated based on 'Species' entry]. Column 'Runabb' is the run abbreviation, which is a unique identifier for a specific study and calculated using 'Speciesabb' and metadata indices. This ensures that each instance (e.g. among instances 130A-N) is separate and uniquely customized. Thus, the output from subsequent studies do not overwrite other studies even if their outputs are saved to the same bucket (e.g. among buckets 135A-N).

User defined metadata includes columns such as 'Assembled'—a Boolean entry recognizing the successful assembly of the study, and 'Notes'—a free-form entry for assembly notes.

Program 115 utilizes a temporary dictionary ('meta_dict') for processing each run. Once the metadata is verified and the data quality is approved, the dictionary is appended to the master metadata database. The following paragraphs provide further detail into the meta_dict.

In meta_dict['Strategy'], this function contains line[index+1] syntax where only two values are acceptable (e.g., RNA-sequence or whole genome sequence). In meta_dict ['Library'], this function contains line[index+2] syntax where any value is acceptable. In meta_dict['Layout'], this function contains (line[index+3])syntax, where only two values are acceptable. In meta_dict['Platform'], this function contains line[index+4] syntax where only one value is acceptable. Program 115 generates a warning if meta_dict ['Platform'] does not have an acceptable value. Program 115 generates a warning if meta_dict['Strategy'] does not have an acceptable value. In meta_dict['Source'], this function contains line[index+5] syntax where only two values are acceptable (e.g., transcriptome or genomic). In meta_dict ['BioSample'], this function contains str(line[index+7]) and 'split' syntaxes. Program 115 generates a warning if meta_dict['BioSample'] does not have an acceptable value. Program 115 generates a warning if meta_dict['Source'] does not have an acceptable value. In meta_dict['Selection'], this function contains(line[index+6]) syntax where any value is acceptable. Program 115 generates a warning if meta_dict ['Layout'] does not have the acceptable values. In meta_dict ['Description'], this function contains str(line[index+7]) and 'split' syntaxes. In meta_dict['TaxID'], this function contains str(line[index+8]) and 'split' syntaxes to ensure TAX ID is an integer. Program 115 generates a warning if meta_dict['TaxID'] is not an integer. In meta_dict['Species'], this function contains str(line[index+10]) and 'split' syntaxes. Program 115 generates the genus and species for an organism when meta_dict['Species'] is performed.

Not all html files are in the same format. To standardize formats across all html files, program 115 determines if 'PRJ' is the value generated when the syntax is str(line [index+11]). In meta_dict['ProjectID'], this function contains str(line[index+12]) and 'split' syntaxes to determine if the value begins with 'PRJ'. Program 115 generates a warning if meta_dict['ProjectID'] generates a value that does not begin with 'PRJ'.

In meta_dict['StudyID'], this function contains str(line [index+14]) and 'split' syntaxes to determine if the identified study) begins with specific prefixes. Program 115 generates a warning if meta_dict['StudyID'] does not begin with the specific prefixes.

In meta_dict['Title'], this function contains str(line[index+15]) syntax where any value is acceptable. For a 'Primary Id', index and str(line) syntaxes are used by program 115 to enumerate(line) if 'Primary Id' in str(line).

In meta_dict['AccessionID'], str(line) and 'split' syntaxes are used by program 115 to determine if accession ID does not match input id. Program 115 raises an exception if the values of the accession ID and input id do not match.

Program 115 applies syntax for abbreviations where def get_correct_size (column, value, size_abbr, desired_size_abbr). If the size of the abbreviation (size_abbr) is equal to the desired size of the abbreviation (desired_size_abbr), then program 115 returns the value from get_correct_size. Additionally, if the size_abbr is 'M' and the desired_size_abbr is 'G', then program 115 applies a correction factor on the value from get_correct_size. If the size_abbr is 'G' and the desired_size_abbr is 'M', then program 115 applies a different correction factor on the value from get_correct_size. Program 115 raises an exception if size abbreviation (size_abbr) is not equal to the desired size abbreviation (desired_size_abbr) or the applied correction factors do not lead to (size_abbr) equal to the desired size abbreviation (desired_size_abbr).

In meta_dict['Spots(M)'], float(str(line[index+3]), multiple 'split', size_abbr, and 'M' syntaxes are used by program 115 to ensure N_READS is a float. The unit of N_READS must be in the millions ('M').

In meta_dict['Bases(Gbp)'], float(str(line[index+6]), multiple 'split', size_abbr, and 'G' syntaxes are used to ensure N_BASES is a float. The unit of N_BASES must be in the billions ('G').

In meta_dict['FileSize(GB)'], float(str(line[index+7]), multiple 'split', size_abbr, and 'G' syntaxes are used to ensure FILESIZE (GB) is a float that is either in gigabytes (GB) or megabytes (MB).

In meta_dict['GC_content'], float(str(line[index+4]) and multiple 'split' syntaxes are used to ensure guanine/cytosine (GC) content is between 20 and 80 percent. Program 115 raises an exception if the GC content is not between 20 and 80 percent, where the exception returns the accession ID and that the GC content is out of bounds.

In meta_dict['DatePublished'], str(line[index+7]) and 'split' syntaxes are used to ensure the date of the study is in the yyyy-mm-dd format and the yyyy>2010. If program 115 determines the study is not in the yyyy-mm-dd format, then program 115 raises an exception.

In meta_dict['ReadLength'], float(str(line[index+11])) and multiple 'split' syntaxes are used to ensure ReadLength is a float equal to or greater than 90. Program 115 raises an exception if the ReadLength is less than 90, where the exception returns a warning that the ReadLength is short.

Example 2—Selection of Cloud Computer Type

Program 115 transforms rows of metadata to launch and run an instance in the cloud by initiating the assembly script. For example, program 115 can determine the type of instance using the variable 'read_length' from the metadata with the following algorithm:

if read_length<=L1:
row_dict['instance_type']=instance_type_1
elif L1<read_length<=L2:
row_dict['instance_type']=instance_type_2
elif L2<read_length<=L3:
row_dict['instance_type']=instance_type_3

Example 3—Customization of Pipeline Scripts

Using a high-level and general-purpose programming language, program 115 imports software libraries, pipeline helper functions, and argument parsers from Example 2. Program 115 can be further customized by selection of pipeline stages. Program 115 uses argument parsers to skip between configured stages, e.g. 'pre-process step 1', 'assembly step 2, and 'post-process step 10'. Program 115 can select which stage is run first and which stage in run last. Additionally, program 115 determines which stages should be run and which stages should not be run. Program 115 can determine if a stage is not one of the configured stages, as entered by a researcher in a command line. When the researcher enters the term "ionization", then program 115 determines that "ionization" is not one of the configured stages. In turn, program 115 raises an exception. Program 115 uses the complete list of stages by default. However, stage selection can be specified during development (e.g., adding, removing, or customizing one or more stages); debugging; or when skipping certain non-essential stages. Example code for verifying the stages input:

def get_stages_to_run(args, stages):
  if args.skip is not None:
    for stage in args.skip:
      if stage not in stages:
        raise Exception('Input skip stage { } not in stages { }'.format(stage, stages))
  if args.first_stage not in stages and args.first_stage is not None:
    raise Exception('Input first_stage { } not in stages { }'.format(args.first_stage, stages))
  if args.last_stage not in stages and args.last_stage is not None:
    raise Exception('Input last_stage { } not in stages { }'.format(args.last_stage, stages))

Example stages include downloading fastq and preprocessing.

At each stage in the assembly pipeline, program 115 utilizes helper functions to determine the success of the stage. Depending on the file format and specific stage, these can include command line syntax functions for (i) measuring the size of the file in bytes; (ii) measuring the number of lines in the file; and (iii) verification of file format.

Program 115 can be configured to send Short Message Service (SMS) notifications to a mobile number. If SMS is activated, text messages are sent by program 115 to a specified mobile number to alert the user as major milestones in the assembly pipeline are completed. Upon failure of an assembly stage, program 115 notifies the mobile phone and automatically terminates the assembly pipeline.

Example 4: Running the Assembly Stage in the Pipeline

The following is example code for the customized Trinity transcriptome assembly and storage stage in the main pipeline script. The automated pipeline herein calls the transcriptome assembler with the script 'run_trinity.sh' (belonging to A2). Each stage is identified, performed and verified with analogous code.

- - -
Run Trinity
- - -

```
stage='trinity'
if stage in stages_to_run:
  print('\n=Stage: { } . . . '.format(stage))
  message=Trinity run'
  cmd='run_trinity.sh'+layout
  run_cmd(cmd)
  verify_results('result')
  send_sms(message)
  save_results_to_cloud_storage('result')
else:
  print('\n { } skipped . . . '.format(stage))
```

Example 5: User Interfaces

In FIG. 6, GUI 600A depicts the warnings contained within the different metadata columns of a fully functional web application supported by program 115. Although GUI 600 does not contain all of the columns described above, GUI 600A is an example of the run abbreviation (RunAbb) in uniquely identifying runs in a way that is user-friendly to the researcher using program 115. Without program 115, using the accession ID is inefficient for the researcher analyzing the transcriptomes. In GUI 600B, the accession IDs that are simultaneously received by program 115 with commas separating the accession IDs are: ERR1924220, ERR1924219, and ERR1924221. The entries in the 'Species' metadata column and 'SpeciesAbb' metadata column for these accession IDs are *Homo sapiens* and Hsapiens, respectively. The entries in 'RunAbb' metadata column are Hsapiens_1 for ERR1924220, Hsapiens_2 for ERR1924219, and Hsapiens_3 for ERR1924221. The entries in the 'Strategy', 'Source', 'Layout', and 'TaxID' metadata columns for each of these accession IDs are: RNA-Seq, TRANSCRIPTOMIC, SINGLE, and 9606, respectively. The entries in the 'Reads(M)' metadata column are: 46.8 for ERR1924220, 63.7 for ERR1924219, and 36.2 for ERR1924221. The entries in the 'GC_content' metadata column are: 46.8 for ERR1924220, 45.6 for ERR1924219, and 47 for ERR1924221. As indicated in the entries in the 'ReadLength' metadata column are: 50 for ERR1924220, 50 for ERR1924219, and 50 for ERR1924221. Program 115 sends the warnings of Read Length 50.0<90 for ERR1924220: Read Length 50.0<90 for ERR1924219; Read Length 50.0<90 for ERR1924221.

In FIG. 6, GUI 600B depicts outputs from downstream analysis. The downstream analysis from program 115 can determine which enzymes a researcher should test. The metadata columns in GUI 600B are: 'QueryID' (the gene used as a query for the search by program 115); 'SubjectID' (the combination of the assembly name and the transcript number from the assembly): 'AssemblyName'; 'ID %'; 'MatchCoverage' (a percentage of the query covered by a match that can also be referred to as a "subject" in the 'SubjectID' or a "hit"); 'Cover*ID' (multiplication product of the 'MatchCoverage' and 'ID'); 'GeneCoverage', 'Has-Gene' (which has a True value if the subject has a full gene and a Negative value if the subject does not have a full gene), and 'GeneLength'. Program 115 uses 'HasGene' to select full genes, some of which Transdecoder fails to predict and identify. Program 115 searches the entries in the following metadata columns for threshold values pertaining to: 'MatchCoverage'; and a minimum ID %, which is in the 'ID %' metadata column. To determine which enzymes should be tested, program 115 uses thresholds for ID % and MatchCoverage Based on the syntax applied and optional machine learning, program 115 determines 'Cover*ID' is the best metric for the hits. In GUI 600B, program 115 receives the query of HomoSapiens_USP30 to generate the following subjects in the 'SubjectID' metadata column: Hsapiens_2_transcript15920: Hsapiens_2_transcript3729; Hsapiens_3_transcript1029: Hsapiens_1_transcript1252; Hsapiens_3_transcript0135; Hsapiens_1_transcript0185: Hsapiens_3_transcript12129; Hsapiens_1_transcript7347; Hsapiens_2_transcript8383; and Hsapiens_1_transcript3573. The assembly for these subjects can be Hsapiens_1, Hsapiens_2, and Hsapiens_3. As noted in the 'SubjectID', the assembly of the subjects and is noted in the name of the subject.

Based on the threshold values, the subjects which meet or exceed the both of the thresholds for 'MatchCoverage' and 'minimum ID %' are: Hsapiens_2_transcript15920; Hsapiens_2_transcript3729: Hsapiens_3_transcript1029; Hsapiens_1_transcript1252; Hsapiens_3_transcript0135; and Hsapiens_3_transcript12129. In turn, program 115 determines the following subjects should be tested further: Hsapiens_2_transcript15920; Hsapiens_2_transcript3729; Hsapiens_3_transcript1029; Hsapiens_1_transcript1252; Hsapiens_3_transcript0135; and Hsapiens_3_transcript12129.

For program 115, other metadata columns can be from BLAST, including alignment length, mismatch, query start, query end, etc.

Example 6: Identified Genes

Program 115 receives a search query and performs the operational steps in flowcharts 200, 300, 40X), and 500 using the syntax and code described above for the automated pipeline herein. The search query is the species name for maize—*Zea mays*. Program 115 is not limited to maize and can be applied to other species which are less or more complex than *Zea mays*. Upon receiving the term "*Zea mays*", program 115 connects to: cloud computing resources in cluster 127: scientific literature periodical databases in cluster 137, such as SciFinder®, Web of Science; and the NCBI webpage in cluster 137. Across over 200 studies, program 115 finds 800 gene variants as a list of potential gene variants. Without having to enter any additional inputs by the researcher, gene variants which have less than 80% identity with the query are automatically removed from the list of potential gene variants. To identify gene variants of interest for experimental study, the list of potential gene variants are further refined based on the GC content and the quality of the transcriptomes by program 115. In Example 6, five transcriptomes are the output generated by program 115 and a new gene variant, which derives from high-quality reads, is identified. Without program 115 in the automated pipeline herein, the researcher would have to manually examine and comb through the individual studies and gene variants to find the new gene variants of interest. Stated another way, the identification of the new gene variant by program 115 obviates tedious analysis of an onerous number of raw data sets associated with complex biological systems, while also identifying new gene variants from high-quality reads. Without program 115 in the automated pipeline herein, the identification of the new gene variant from high-quality reads would take on the order of several days or even weeks by a researcher who is an expert in bioinformatics. In contrast, program 115 in the automated pipeline herein, the identification of the new gene variant takes on the order of two to three hours by the same researcher who is an expert in bioinformatics. Program 115 applies machine learning for similar species to *Zea mays* in terms of transcriptomic similarity to identify gene variants in the similar species to *Zea mays*. The machine learning can modify the threshold for the criterion in determining high quality reads for different species based on baseline determination, such as the identification of gene variants for *Zea mays*. Further, the new threshold allows program 115 to maintain the efficiency and efficacy in which new gene variants are identified.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for parallel processing of raw data sets directed to complex systems, the method comprising:
   connecting to databases containing the raw data sets;
   receiving a query and thereby identifying studies and extracting accession identifications from the identified studies;
   simultaneously submitting the respective accession identifications to respective cloud computing instances customized for each of the identified studies, and thereby triggering an assembly pipeline for outputting refinements for each of the studies;
   retrieving metadata from the accession identifications, wherein the metadata comprises one or more values describing the study associated with the accession identifications;
   applying a set of commands on the one or more values of the metadata, wherein the set of commands identifies errors in the metadata;
   correcting the errors in the metadata, wherein the metadata is associated with the outputted refinements;
   sending the outputted refinements for each of the studies to respective cloud computing buckets;
   in response to sending the outputted refinements for each of the studies to the respective cloud computing buckets, identifying gene variants based on the outputted refinements;
   in response to identifying the gene variants, displaying the outputted refinements in the one or more columns in a graphical user-interface; and
   wherein the outputted refinements comprise transcriptomes, proteomes, genomes, and metabolomes.

2. The method of claim 1, wherein simultaneously submitting the respective accession identifications to the respective cloud computing instances customized for each of the identified studies, comprises:
   converting the metadata into scripting parameters and hardware parameters and thereby customizing the assembly pipeline; and
   determining an ideal cloud computing instance for each of the identified studies.

3. The method of claim 2, wherein customizing the assembly pipeline comprises:
   processing scripts within the assembly pipeline in series; and
   sending the processed scripts to the ideal cloud computing instances.

4. The method of claim 3, wherein processing the scripts within the assembly pipeline in series comprises:
   downloading datasets;
   performing pre-processing steps;
   implementing a transcriptome assembly for generating transcriptomes;
   performing quality control functions on the downloaded datasets and the generated transcriptomes; and
   performing downstream analysis steps.

5. The method of claim 4, wherein the downstream analysis steps comprise: detection of single copy orthologs, open reading frames (ORFs), gene quantification, and annotation.

6. The method of claim 1, wherein sending the outputted refinements for each of the studies to the respective cloud computing instances comprises:
   comparing predicted peptides to gene queries to identify the gene variants;
   sending the identified gene variants to the respective cloud computing buckets for storage;
   extracting metadata of the identified gene variants;
   validating the identified gene variants by three-dimensional (3D) modeling and experimental findings; and
   wherein the outputted refinements are transcriptomes.

7. The method of claim 6, wherein analyzing the identified gene variant comprises:
   combining the metadata of the identified gene variants and the analyzed identified gene variants with metadata of the transcriptomes; and
   thereby measuring quality of the transcriptomes.

8. The method of claim 7, wherein measuring the quality of the transcriptomes comprises:
   applying machine learning on the metadata of the identified gene variants;
   generating a model directed to un-analyzed transcriptomes using the applied machine learning; and
   selecting additional studies of interest based on the generated model.

9. The method of claim 4, wherein the pre-processing steps comprise: unzipped version
   of the raw data, bad read removal, trim read adaptors, and formatted read names.

10. A system for parallel processing of raw data sets directed to complex systems, the system comprising:
    a server;
    a computing device in communication with the server over a network, the computing device including a processor and a memory, the memory bearing computer executable code configured to perform the steps of:

connecting to databases containing the raw data sets;
receiving a query and thereby identifying studies and extracting accession identifications from the studies;
identifying studies containing the term;
extracting respective accession identifications from the identified studies;
simultaneously submitting the respective accession identifications to respective cloud computing instances customized for each of the identified studies, and thereby triggering an assembly pipeline for outputting refinements for each of the studies;
retrieving metadata from the accession identifications, wherein the metadata comprises one or more values describing the study associated with the accession identifications;
applying a set of commands on the one or more values of the metadata, wherein the set of commands identifies errors in the metadata;
correcting the errors in the metadata, wherein the metadata is associated with the outputted refinements;
sending the outputted refinements for each of the studies to respective cloud computing buckets;
in response to sending the outputted refinements for each of the studies to the respective cloud computing buckets, identifying gene variants based on the outputted refinements;
in response to identifying the gene variants, displaying the outputted refinements in the one or more columns in a graphical user-interface; and
wherein the outputted refinements comprise transcriptomes, proteomes, genomes, and metabolomes.

11. The system of claim 10, wherein simultaneously submitting the respective accession identifications to the respective cloud computing instances customized for each of the identified studies, comprises:
converting the metadata into scripting parameters and hardware parameters and thereby customizing the assembly pipeline; and
determining an ideal cloud computing instance for each of the identified studies.

12. The system of claim 11, wherein customizing the assembly pipeline comprises: processing scripts within the assembly pipeline in series; and sending the processed scripts to the ideal cloud computing instances.

13. The system of claim 12, wherein processing the scripts within the assembly pipeline in series comprises:
downloading datasets;
performing pre-processing steps;
implementing a transcriptome assembly for generating transcriptomes;
performing quality control functions on the downloaded datasets and the generated transcriptomes; and
performing downstream analysis steps.

14. The system of claim 13, wherein the downstream analysis steps comprise: detection of single copy orthologs, open reading frames (ORFs), gene quantification, and annotation.

15. The system of claim 10, wherein sending the outputted refinements for each of the studies to the respective cloud computing instances comprises:
comparing predicted peptides to gene queries to identify the gene variants;
sending the identified gene variants to the respective cloud computing buckets for storage;
extracting metadata of the identified gene variants;
validating the identified gene variants by three-dimensional (3D) modeling and experimental findings; and
wherein the outputted refinements are transcriptomes.

16. A computer program product for parallel processing of raw data sets directed to complex systems comprising computer executable code embodied in a non-transitory computer readable medium that, when executing on one or more computing devices, performs steps of:
connecting to databases containing the raw data sets;
receiving a query and thereby identifying studies and extracting accession identifications from the studies;
identifying studies containing the term;
extracting respective accession identifications from the identified studies;
simultaneously submitting the respective accession identifications to respective cloud computing instances customized for each of the identified studies, and thereby triggering an assembly pipeline for outputting refinements for each of the studies;
retrieving metadata from the accession identifications, wherein the metadata comprises one or more values describing the study associated with the accession identifications;
applying a set of commands on the one or more values of the metadata, wherein the set of commands identifies errors in the metadata;
correcting the errors in the metadata, wherein the metadata is associated with the outputted refinements;
sending the outputted refinements for each of the studies to respective cloud computing buckets;
in response to sending the outputted refinements for each of the studies to the respective cloud computing buckets, identifying gene variants based on the outputted refinements;
in response to identifying the gene variants, displaying the outputted refinements in the one or more columns in a graphical user-interface; and
wherein the outputted refinements comprise transcriptomes, proteomes, genomes, and metabolomes.

17. The system of claim 16, wherein simultaneously submitting the respective accession identifications to the respective cloud computing instances customized for each of the identified studies, comprises:
converting the metadata into scripting parameters and hardware parameters and thereby customizing the assembly pipeline; and
determining an ideal cloud computing instance for each of the identified studies.

18. The system of claim 17, wherein customizing the assembly pipeline comprises:
processing scripts within the assembly pipeline in series; and
sending the processed scripts to the ideal cloud computing instance.

19. The system of claim 18, wherein processing the scripts within the assembly pipeline in series comprises:
downloading datasets;
performing pre-processing steps;
implementing a transcriptome assembly for generating transcriptomes;
performing quality control functions on the downloaded datasets and the generated transcriptomes; and
performing downstream analysis steps.

20. The system of claim 19, wherein the downstream analysis steps comprise: detection of single copy orthologs, open reading frames (ORFs), gene quantification, and annotation.

* * * * *